United States Patent
Tsou et al.

(10) Patent No.: US 11,174,520 B2
(45) Date of Patent: Nov. 16, 2021

(54) **METHOD FOR DETECTING PRESENCE OR ABSENCE OF *MYCOBACTERIUM* AND KIT THEREOF**

(71) Applicant: DELTA ELECTRONICS, INC., Taoyuan (TW)

(72) Inventors: Chih-Cheng Tsou, Taoyuan (TW);
Min-Hsien Wu, Taoyuan (TW);
Wen-Pin Chou, Taoyuan (TW);
Hsin-Yao Wang, Taoyuan (TW);
Chien-Ru Lin, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 158 days.

(21) Appl. No.: 16/287,585

(22) Filed: Feb. 27, 2019

(65) Prior Publication Data
US 2019/0264261 A1   Aug. 29, 2019

Related U.S. Application Data

(60) Provisional application No. 62/715,809, filed on Aug. 8, 2018.

(30) Foreign Application Priority Data

Feb. 27, 2018   (CN) .......................... 201810161343.4
Oct. 25, 2018   (CN) .......................... 201811251147.2

(51) Int. Cl.
*C12Q 1/689*   (2018.01)
*C12Q 1/6883*   (2018.01)

(52) U.S. Cl.
CPC .......... *C12Q 1/689* (2013.01); *C12Q 1/6883* (2013.01); *C12Q 2600/158* (2013.01)

(58) Field of Classification Search
None
See application file for complete search history.

(56) References Cited

U.S. PATENT DOCUMENTS 5,554,503 A    9/1996  Down et al.
8,044,184 B2 * 10/2011  Ishikawa ................ C12Q 1/689
                                                          536/23.1
(Continued)

FOREIGN PATENT DOCUMENTS

CN    101168780 A    4/2008
CN    102414326      4/2012
(Continued)

OTHER PUBLICATIONS

Plant-Microbe Genomics Facility (PMGF) at The Ohio State University ("OSU"), "Procedures and Recommendations for Quantitative PCR", version 1.2 (Apr. 2003). (Year: 2003).*
Annual Report, WHO 2017, "Bending the Curve ending TB", 76 pages.
Behr, Ma et al., "Transmission of *Mycobacterium tuberculosis* from Patients Smear-Negative for Acid-Fast Bacilli", Lancet, 1999, 6:444-9.
(Continued)

*Primary Examiner* — Diana B Johannsen
(74) *Attorney, Agent, or Firm* — Hauptman Ham, LLP (57) ABSTRACT

A method and a kit for detecting mycobacterium are provided. The method includes steps of: providing a sample; providing a pair of primers, which is selected from a group consisting of a sequence having about 45% to 100% similar to SEQ ID NO. 1, a sequence having about 60% to 100% similar to SEQ ID NO. 2, a sequence complementary thereof; performing a polymerase chain reaction by using the set of primers and the sample to obtain a product; and analyzing the product to detect the presence of the mycobacterium.

7 Claims, 6 Drawing Sheets

Specification includes a Sequence Listing.

(56) References Cited

U.S. PATENT DOCUMENTS

| | | |
|---|---|---|
| 9,145,591 B1 | 9/2015 | Exner |
| 2008/0241826 A1 | 10/2008 | Ishikawa |

FOREIGN PATENT DOCUMENTS

| | | | | |
|---|---|---|---|---|
| CN | 102471806 A | 5/2012 | | |
| CN | 102533959 A | 7/2012 | | |
| CN | 102808031 A | 12/2012 | | |
| TW | 201102436 A | 1/2011 | | |
| TW | I392740 | 4/2013 | | |
| TW | 201408779 A | 3/2014 | | |
| TW | 201439112 | 10/2014 | | |
| WO | WO-9947706 A1 * | 9/1999 | ........... | C12Q 1/6874 |
| WO | 2005103249 A1 | 11/2005 | | |
| WO | 2017077999 A1 | 5/2017 | | |

OTHER PUBLICATIONS

Djelouadji, Zoheira et al., A Single-Step Sequencing Method for the Identification of *Mycobacterium tuberculosis* Complex Species. PLoS NeglTrop Dis. 2008.18:e253.

Babafemi, Emmanuel O. et al., "Effectiveness of real-time polymerase chain reaction assay for the detection of *Mycobacterium tuberculosis* in pathological samples: a systematic review and meta-analysis." Syst Rev. 2017.25:215.

Turner, Richard D., et al., "Tuberculosis Infectiousness and Host Susceptibility." J Infect Dis. 2017.216:S636-S643. Review.

Maeda, E., et al., "Method for detection of variable Number of tandem repeats numbers and insertion of IS6110 into QUB11a loci in *Mycrpbacterium tuberculosis* isolates", Oct. 3, 2014; *Mycobacterium tuberculosis* DNA, insertion sequence:IS6110, VNTR, complete sequence, strain: F309; pp. 1-2.

* cited by examiner

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: forward primer

<400> SEQUENCE: 1
ctcggctagt gcattgtcat a                                         21

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
ctcgacctga aagacgttat cc                                        22

<210> SEQ ID NO 3
<211> LENGTH: 24
<212> TYPE: DNA
<213> ORGANISM: Artificial Sequence
<220> FEATURE:
<223> OTHER INFORMATION: probe

<400> SEQUENCE: 3
agtacacatc gatccggttc agcg                                      24

<210> SEQ ID NO 4
<211> LENGTH: 141
<212> TYPE: DNA
<213> ORGANISM: Mycobacterium tuberculosis

<400> SEQUENCE: 4
ctcggctagt gcattgtcat aggagcttcc gaccgctccg accgacggtt ggatgcctgc    60
ctcggcgagc cgctcgctga accggatcga tgtgtactga gatcccctat ccgtatggtg   120
gataacgtct ttcaggtcga g                                            141

<210> SEQ ID NO 5
<211> LENGTH: 22
<212> TYPE: DNA
<213> ORGANISM: Artificial Sequence
<220> FEATURE:
<223> OTHER INFORMATION: probe
```

```
<400> SEQUENCE: 5
tctcagtaca catcgatccg gt                                              22

<210> SEQ ID NO 6
<211> LENGTH: 900
<212> TYPE: DNA
<213> ORGANISM: Mycobacterium tuberculosis

<400> SEQUENCE: 6
gctcaacgga acattcaacc caaacggatg aaccgccccg gtgagtccgg agactctctg      60
atctgagacc tcagccggcg gctggtctct ggcgttgagc gtagtaggca gcctcgagtt     120
cgaccggcgg gacgtcgccg cagtactggt agaggcggcg atggttgaac cagtcgaccc     180
agcgcgcggt ggccaactcg acatcctcga tggaccgcca gggcttgccg ggtttgatca     240
gctcggtctt gtataggccg ttgatcgtct cggctagtgc attgtcatag gagcttccga     300
ccgctccgac cgacggttgg atgcctgcct cggcgagccg ctcgctgaac cggatcgatg     360
tgtactgaga tccctatcc gtatggtgga taacgtcttt caggtcgagt acgccttctt      420
gttggcgggt ccagatggct tgctcgatcg cgtcgaggac catggaggtg gccatcgtgg     480
aagcgacccg ccagcccagg atcctgcgag cgtaggcgtc ggtgacaaag gccacgtagg     540
cgaaccctgc ccaggtcgac acataggtga ggtctgctac ccacagccgg ttaggtgctg     600
gtggtccgaa gcggcgctgg acgagatcgg cgggacgggc tgtggccgga tcagcgatcg     660
tggtcctgcg ggctttgccg cgggtggtcc cggacaggcc gagtttggtc atcagccgtt     720
cgacggtgca tctggccacc tcgatgccct cacggttcag ggttagccac actttgcggg     780
caccgtaaac accgtagttg gcggcgtgga cgcggctgat gtgctccttg agttcgccat     840
cgcgcagctc gcggcggctg ggctcccggt tgatgtggtc gtagtaggtc gatgggcga      900
```

METHOD FOR DETECTING PRESENCE OR ABSENCE OF *MYCOBACTERIUM* AND KIT THEREOF

CROSS-REFERENCE TO RELATED APPLICATION

This application claims priority to China Application Serial Number 201810161343.4, filed on Feb. 27, 2018, U.S. Provisional Application Ser. No. 62/715,809 filed on Aug. 8, 2018, and China Application Serial Number 201811251147.2, filed on Oct. 25, 2018, the disclosures of which are incorporated herein by reference in their entireties.

BACKGROUND

Field of Invention

The present invention relates to a detecting method and kit thereof. More particularly, the present invention relates to a method for detecting mycobacterium and kit thereof.

Description of Related Art

*Mycobacterium* can be divided into *Mycobacterium tuberculosis* complex (MTBC) and non-tuberculous mycobacterium (NTM). Some pathogens of tuberculosis belong to MTBC bacteria, such as *M. africanum, M. bovis, M. caprae, M. canettii, M. microti, M. pinnipedii* and *M. tuberculosis*. These pathogens can cause tuberculosis in humans or animals, wherein *M. africanum, M. bovis* and *M. tuberculosis* are the main strains of human tuberculosis.

Tuberculosis can occur in any organ or tissue, such as lungs, lymph nodes, meninges, pleura, kidneys, bones, skin, digestive tract, and genitourinary tract, etc. Tuberculosis can almost heal if the patient receives the treatment with the anti-tuberculosis drug in early stage. However, if the patient does not receive the treatment in early stage, the patient will have about half of the death rate in three years. Therefore, a method is need for detecting whether the patient is infected by the MTBC or not in the early stage of the clinical infection, and the method is important for improving the cure rate of the disease.

SUMMARY

The present disclosure provides a method for detecting mycobacterium including steps of: providing a sample; providing a pair of primers, wherein the primers are selected from the group consisting of SEQ ID NO. 1, SEQ ID NO. 2, a sequence having about 45% to about 99% similar to SEQ ID NO. 1, a sequence having about 60% to about 99% similar to SEQ ID NO. 2, a sequence complementary to SEQ ID NO. 1, and a sequence complementary to SEQ ID NO. 2; performing a polymerase chain reaction (PCR) by using the primers and the sample to obtain a product; and analyzing the product to detect the presence of the mycobacterium.

In one embodiment, the step of providing the sample includes a step of providing a clinical sample including *Mycobacterium tuberculosis* complex (MTBC).

In one embodiment, the clinical sample is blood, sputum, bronchoalveolar lavage fluid, urine, feces, or a combination thereof.

In one embodiment, the step of performing the PCR by using the primers and the sample to obtain the product includes amplifying a portion of IS6110 sequence in MTBC by the PCR to obtain the product, wherein the portion of IS6110 sequence is SEQ ID NO. 4.

In one embodiment, the method further includes a step of providing a probe; wherein the probe is selected from the group consisting of SEQ ID NO. 3, a sequence having about 70% to about 99% similar to SEQ ID NO. 3, and a sequence complementary to SEQ ID NO. 3.

In one embodiment, before the step of performing the PCR by using the primers and the sample to obtain the product, the method further includes hybridizing the probe to the sample.

In one embodiment, the PCR in the step of performing the PCR by using the primers and the sample to obtain the product is a real-time quantitative PCR (real-time PCR).

The present disclosure also provides a kit for detecting mycobacterium including a pair of primers, wherein the primers are selected from the group consisting of SEQ ID NO. 1, SEQ ID NO. 2, a sequence having about 45% to about 99% similar to SEQ ID NO. 1, a sequence having about 60% to about 99% similar to SEQ ID NO. 2, a sequence complementary to SEQ ID NO. 1, and a sequence complementary to SEQ ID NO. 2.

In one embodiment, the primers are SEQ ID NO. 1 and SEQ ID NO. 2.

In one embodiment, the kit further includes a probe, wherein the probe is selected form the group consisting of SEQ ID NO. 3, a sequence having about 70% to about 99% similar to SEQ ID NO. 3, and a sequence complementary to SEQ ID NO. 3.

In one embodiment, the probe is SEQ ID NO. 3.

In one embodiment, the kit further includes a clinical sample, wherein the clinical sample is blood, sputum, bronchoalveolar lavage fluid, urine, feces, or a combination thereof.

In one embodiment, the kit further includes a target gene, wherein the target gene is IS6110 sequence of MTBC.

In one embodiment, the kit further includes a template, wherein the template has about 100 to about 250 base pairs.

In one embodiment, the template is SEQ ID NO. 4.

It is to be understood that both the foregoing general description and the following detailed description are by examples, and are intended to provide further explanation of the invention as claimed.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides detailed description of many different embodiments, or examples, for implementing different features of the provided subject matter. These are, of course, merely examples and are not intended to limit the invention but to illustrate it. In addition, various embodiments disclosed below may combine or substitute one embodiment with another, and may have additional embodiments in addition to those described below in a beneficial way without further description or explanation. In the following description, many specific details are set forth to provide a more thorough understanding of the present disclosure. It will be apparent, however, to those skilled in the art, that the present disclosure may be practiced without these specific details.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

The present disclosure provides a method for detecting mycobacterium including following steps. A sample, a pair of primers (also called a primer pair) and a probe are provided. The primers are selected form the group consisting of SEQ ID NO. 1, SEQ ID NO. 2, a sequence having about 45% to about 99% similar to SEQ ID NO. 1, a sequence having about 60% to about 99% similar to SEQ ID NO. 2, a sequence complementary to SEQ ID NO. 1, and a sequence complementary to SEQ ID NO. 2. The probe is selected from the group consisting of SEQ ID NO. 3, a sequence having about 70% to about 99% similar to SEQ ID NO. 3, and a sequence complementary to SEQ ID NO. 3. Then, a polymerase chain reaction (PCR) is performed by using the primers, the probe, and the sample to obtain a product. Finally, the product is analyzed to detect the presence of the mycobacterium.

The sample includes a clinical sample from different sources, such as blood, sputum, bronchoalveolar lavage fluid, urine, feces, or a combination thereof. In one embodiment, the clinical sample including *Mycobacterium tuberculosis* complex (MTBC).

The primers as above-mentioned are selected from, but not limited to, SEQ ID NOs. 1 and 2. The primers can be selected from not only the complement of SEQ ID NO. 1 and the complement of SEQ ID NO. 2, but also some degrees of sequence variation in SEQ ID NOs. 1 and 2. In other words, the sequence having 45% to 99% similar to SEQ ID NO. 1 and the sequence having 60% to 99% similar to SEQ ID NO. 2 can also provide the same effect in the present embodiment. In some examples, the primers are selected from a degenerate sequence of SEQ ID NO. 1 and a degenerate sequence of SEQ ID NO. 2. The term "degenerate sequence" refers to that a portion of nucleotides of the oligonucleotide sequence in the present disclosure is replaced by other nucleotides. In other words, the degenerate sequence of SEQ ID NO. 1 refers to that when the sequence length of the SEQ ID NO. 1 is constant, the oligonucleotide sequence having about 1% to 55% variation can be tolerated. The degenerate sequence of SEQ ID NO. 2 refers to that when the sequence length of the SEQ ID NO. 2 is constant, the oligonucleotide sequence having about 1% to 40% variation can be tolerated. In some examples, the primers are selected from a derived sequence of SEQ ID NO. 1 and a derived sequence of SEQ ID NO. 2. The term "derived sequence" refers to that 3' end and/or 5' end of the oligonucleotide sequence in the present disclosure is modified, and part or all of the oligonucleotide sequence can be reserved. In other words, the derived sequence of SEQ ID NO. 1 refers to that when the sequence length of the SEQ ID NO. 1 is increased or decreased, the oligonucleotide sequence having about 1% to 55% variation can be tolerated. The derived sequence of SEQ ID NO. 2 refers to that when the sequence length of the SEQ ID NO. 1 can be increased or decreased, the oligonucleotide sequence having about 1% to 40% variation can be tolerated. In other embodiments, the primers are selected from the group consisting of a sequence having about 80% to about 99% similar to SEQ ID NO. 1 and a sequence having about 80% to about 99% similar to SEQ ID NO. 2.

The probe as above-mentioned is selected from, but not limited to, SEQ ID NO. 3. The probe can be selected from not only the complement of SEQ ID NO. 3, but also some degrees of sequence variation in SEQ ID NO. 3. In other words, the sequence having 70% to 99% similar to SEQ ID NO. 3 can also provide the same effect in the present embodiment. In some examples, the probe is selected from a degenerate sequence of SEQ ID NO. 3. The degenerate sequence of SEQ ID NO. 3 refers to that when the sequence length of the SEQ ID NO. 3 is constant, the oligonucleotide sequence having about 1% to 30% variation can be tolerated. In other examples, the probe is selected from a derived sequence of SEQ ID NO. 3. The degenerate sequence of SEQ ID NO. 3 refers to that 3' end and/or 5' end of the oligonucleotide sequence in the present disclosure is increased or decreased, the oligonucleotide sequence having about 1% to 30% variation can be tolerated. In other embodiments, the probe is selected from the group consisting of a sequence having about 80% to about 99% similar to SEQ ID NO. 3.

In one embodiment, performing a polymerase chain reaction (PCR) by using the primers, the probe, and the sample to obtain a product includes amplifying a portion of IS6110 sequence in MTBC by the PCR to obtain the product, wherein the portion of IS6110 sequence is SEQ ID NO. 4. The PCR is a technology of molecular biology, and a specific deoxyribonucleic acid (DNA) fragment is amplified by a primer pair having oligonucleotide sequence. It will be understood that the sequences disclosed in the present disclosure can be used in every kinds of the PCR as a base technology. In one example, the PCR includes, but not limited to, real-time PCR. In one example, if the real-time PCR is a probe system (sequence-specific DNA probes), a step before performing the PCR by using the primers and the sample further includes hybridizing the probe to the sample, such that the probe anneals to the target sequence. That is, the PCR is performed by the primers, the probe, and the sample to obtain the product.

The present disclosure provides a kit for detecting mycobacterium including a pair of primers and a probe. The primers are selected from the group consisting of SEQ ID NO. 1, SEQ ID NO. 2, a sequence having about 45% to about 99% similar to SEQ ID NO. 1, a sequence having about 60% to about 99% similar to SEQ ID NO. 2, a sequence complementary to SEQ ID NO. 1, and a sequence complementary to SEQ ID NO. 2. In some embodiments, the primers are SEQ ID NO. 1 and SEQ ID NO. 2. In some embodiments, the primers are the sequence having about 45% to about 99% similar to SEQ ID NO. 1 and the sequence having about 60% to about 99% similar to SEQ ID NO. 2. In some embodiments, the primers are the sequence complementary to SEQ ID NO. 1 and the sequence complementary to SEQ ID NO. 2. The probe is selected form the group consisting of SEQ ID NO. 3, a sequence having about 70% to about 99% similar to SEQ ID NO. 3, and a sequence complementary to SEQ ID NO. 3. In some embodiments, the probe is SEQ ID NO. 3. In some embodiments, the probe is the sequence having about 70% to about 99% similar to SEQ ID NO. 3. In some embodiments, the probe is the sequence complementary to SEQ ID NO. 3.

In other embodiments, the kit for detecting mycobacterium further includes a clinical sample. The clinical sample is blood, sputum, bronchoalveolar lavage fluid, urine, feces, or a combination thereof. For example, the kit for detecting mycobacterium can be used in every medical unit, and subject's (e.g. human) body fluids or excretions are collected for detection by the kit.

In some embodiment, the kit for detecting mycobacterium further includes a target gene, and the target gene is IS6110 sequence of MTBX. In some embodiment, the kit for detecting mycobacterium further includes a template having about 100 to about 250 base pairs. For example, the template can be a portion of IS6110 sequence, such as SEQ ID NO. 4, having 141 base pairs. But in other embodiments, the template does not include the sequence as set forth in SEQ ID NO. 4. The template has an artificial sequence with about 100 to about 250 base pairs, which can be annealed and amplified by the primers of the present disclosure. In some embodiment, the sequence as set forth in SEQ ID NO. 4 can be directly inserted into different vectors. When the vector having SEQ ID NO. 4 as template is amplified, the specificity of the detection is high and the performance of the detection is excellent.

The following examples are for verifying that the presence of the mycobacterium can be detected in various embodiments of the present disclosure. It should be noted that the following examples are provided for illustration only and are not intended to limit the present disclosure.

The Design of Primers and Probe

IS6110 sequence of the MTBX is highly conservative, so the design of primers and probe of the example were based on online design program, such as "primer 3" and "GenScript Real-time PCR Primer Design", for IS6110 sequence of the MTBX (GenBank: LC005482).

Figure 1:
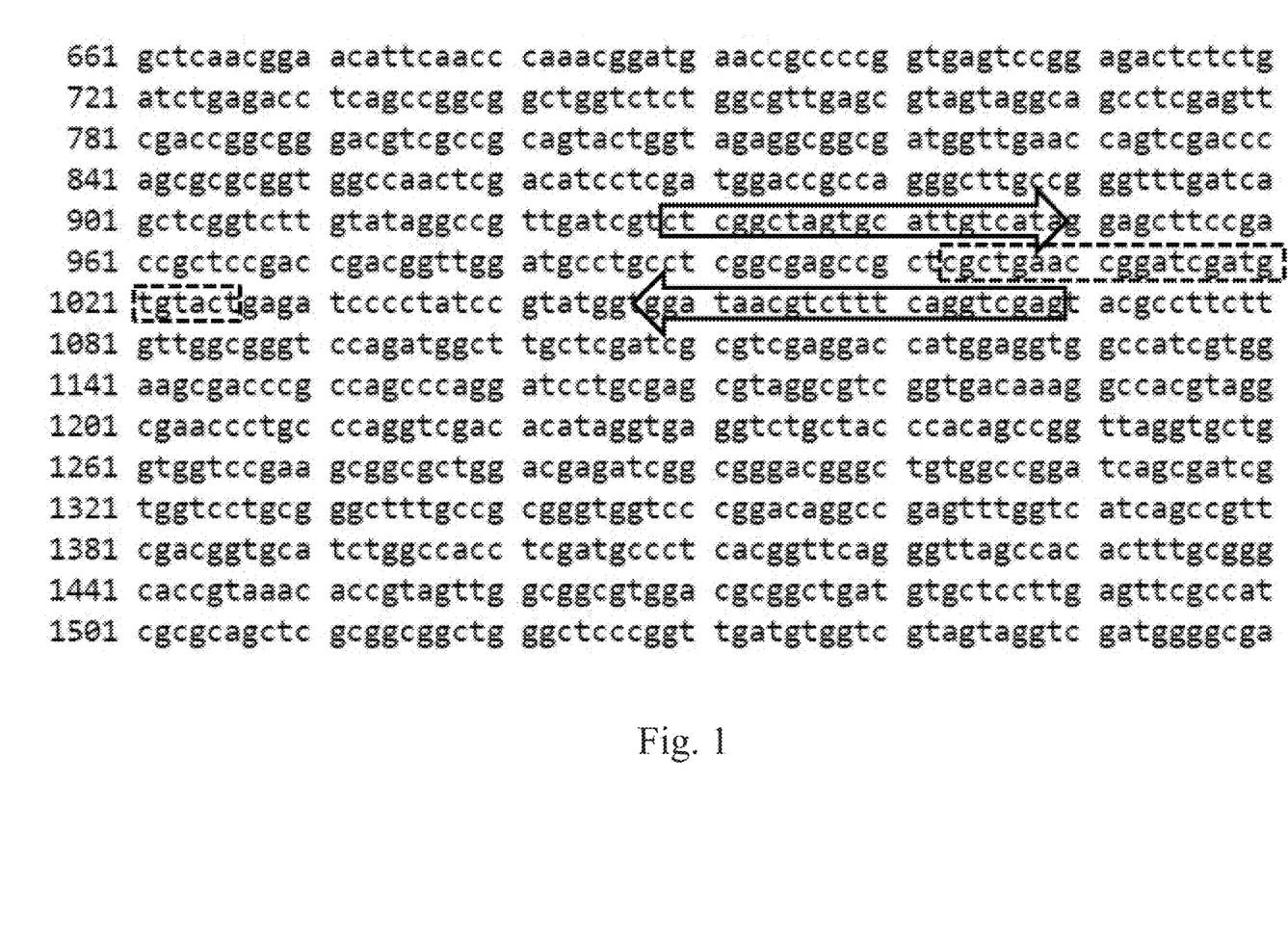
FIG. 1 is depicted the design locations of the primers and probe in the portion of IS6110 sequence according to one embodiment of the present disclosure. The portion of IS6110 sequence is DNA obtained from *Mycobacterium tuberculosis*, and has 900 base pairs as set forth in SEQ ID NO: 6.

According to the information of Accession No. LC005482 provided by the GenBank library, FIG. 1 shows a portion of a forward sequence of the IS6110 sequence. The primers of the example were SEQ ID NO. 1 and SEQ ID NO. 2. The nucleotide sequence as set forth in SEQ ID NO. 1 was designed based on 929-949 base pair of IS6110 sequence (surrounded by right arrow). The nucleotide sequence as set forth in SEQ ID NO. 2 was designed based on 1048-1069 base pair of IS6110 sequence (surrounded by left arrow). The nucleotide sequence as set forth in SEQ ID NO. 3 was designed based on IS6110 sequence from 929 to 1069 base pair (surrounded by dotted box). Therefore, the product amplified by the primers SEQ ID NOs. 1 and 2 had a length of 141 base pairs.

Analyzing the Sensitivity of Primers

According to the sequence showed in GenBank library Accession No. LC005482 as above-mentioned, it was cloned into pUC57 vector (Protech CO., Ltd, GenBank: Y14837.1) to obtain a standard plasmid with IS6110 sequence (hereinafter IS6110 standard plasmid).

According to the commercial real-time PCR kit (QuantiNova Probe PCR Kit, Qiagen) product manual, the reaction mixture contained a template (IS6110 standard plasmid), 15 µL of a real-time PCR reagent (QuantiNova probe master mix), a primer pair with a concentration of 1000 nM (667 nM of SEQ ID NO. 1 and 333 nM of SEQ ID NO. 2), and 27 nM of a probe (SEQ ID NO. 3) to prepare the reaction mixture with a total volume of 30 µL. The conditions of the real-time PCR were denaturation at 95° C. for 5 seconds and annealing/amplification at 60° C. for 10 seconds, and the reaction mixture was placed in a real-time PCR reactor (CFX-96, BioRad) for 45 cycles of reaction.

Figure 2:
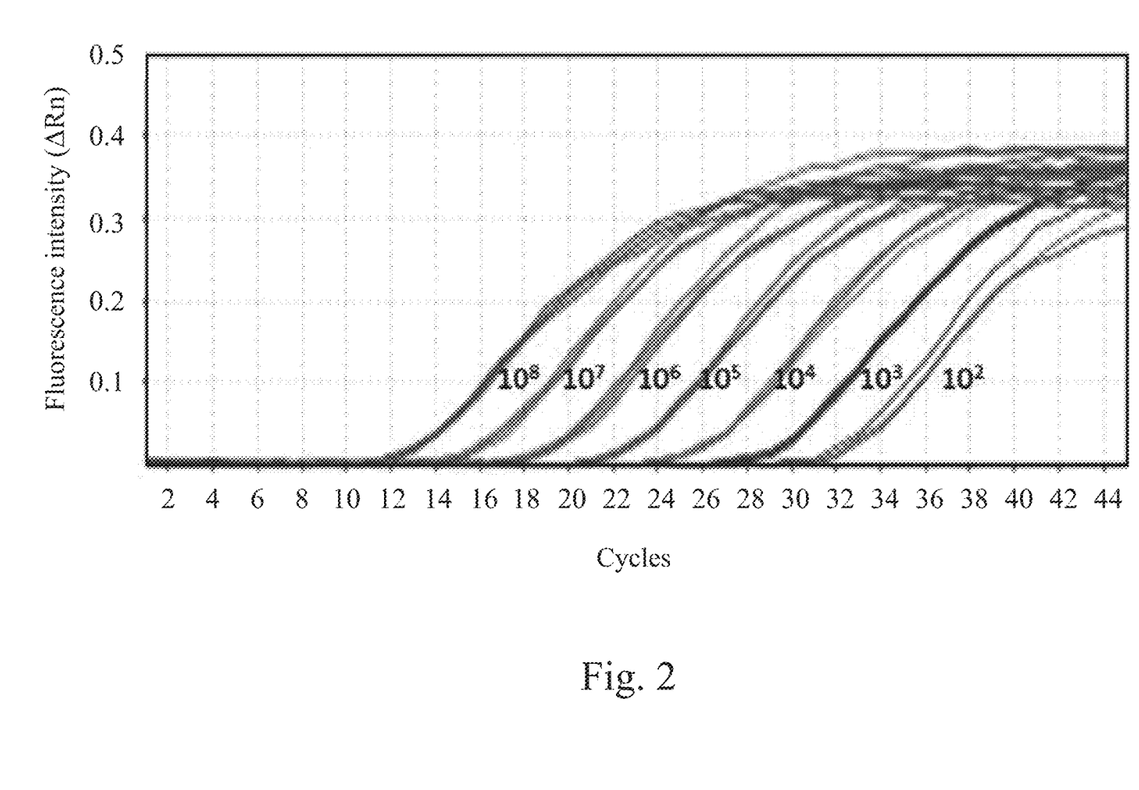
FIG. 2 shows the amplification curve of the real-time PCR with the primers SEQ ID NOs. 1 and 2, and the primers were tested under a different amount of templates according to one embodiment of the present disclosure.
Figure 3:
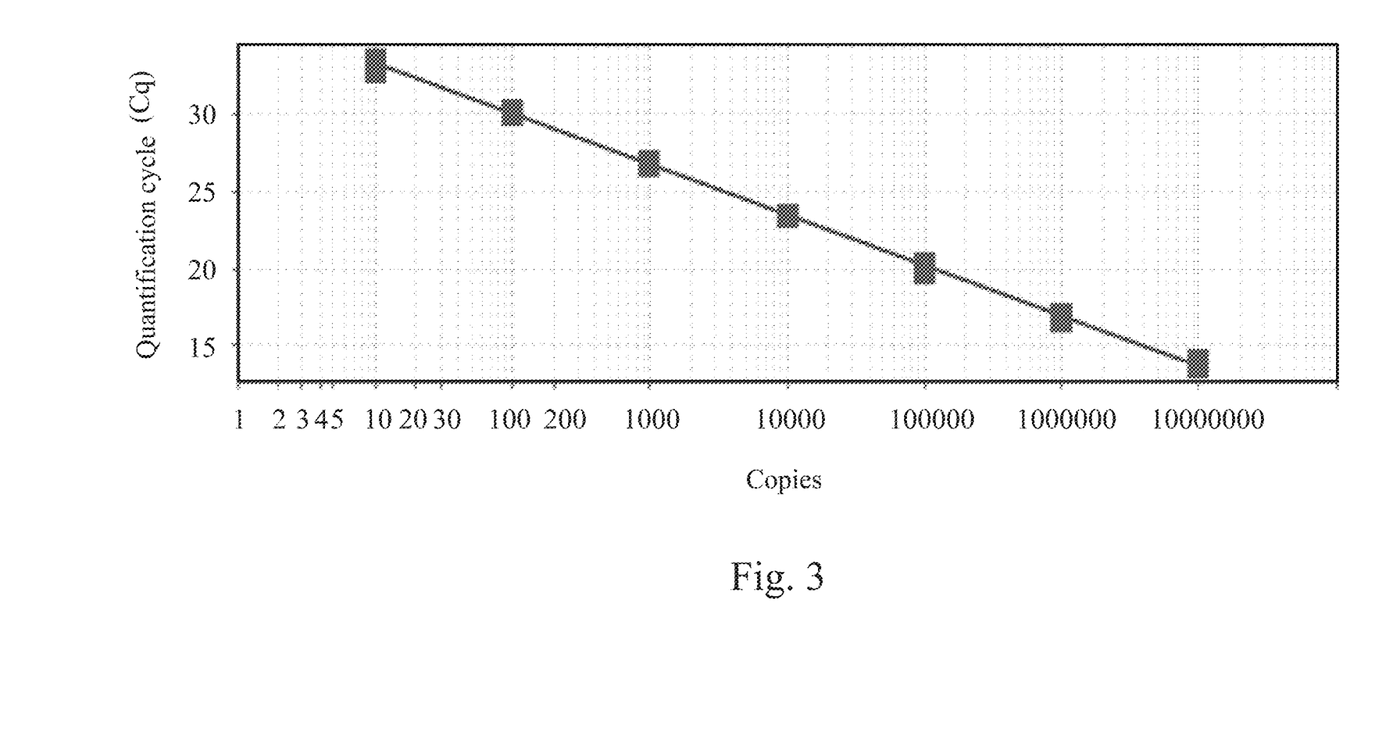
FIG. 3 based on FIG. 2 shows the standard curve of templates having different initiated amount according to one embodiment of the present disclosure.

It should be noted that in this example, the real-time PCR was performed with different amounts of the template for testing the sensitivity of the primers SEQ ID NOs. 1 and 2. The formulation of the reaction mixture as above-mentioned, 8 groups respectively containing different amounts of the templates were prepared, such as IS6110 standard plasmid with $10^1$, $10^2$, $10^3$, $10^4$, $10^5$, $10^6$, $10^7$ and $10^8$ copies. Each of the groups respectively containing $10^2$, $10^3$, $10^4$, $10^5$, $10^6$, $10^7$ and $10^8$ copies were performed the real-time PCR as above-mentioned, and each group was repeated three times. As shown in FIGS. 2 and 3 are respectively an amplification curve and a standard curve obtained after performing the real-time PCR. As shown in FIG. 2, the horizontal axis is the number of cycles, and the vertical axis is the fluorescence intensity ($\Delta$Rn). The amplification curve shows that all of the fluorescence values from $10^2$ to $10^8$ copies show a positive trend of rising. As shown in Table 1 below, the quantification cycle (Cq) values of $10^2$, $10^3$, $10^4$, $10^5$, $10^6$, $10^7$ and $10^8$ copies are respectively 33.19, 30.08, 26.75, 23.35, 19.99, 16.72, and 13.88.

TABLE 1

| | Copies | | | | | | |
|---|---|---|---|---|---|---|---|
| | $10^2$ | $10^3$ | $10^4$ | $10^5$ | $10^6$ | $10^7$ | $10^8$ |
| Cq value | 33.19 | 30.08 | 26.75 | 23.35 | 19.99 | 16.72 | 13.88 |

Continuing with FIG. 3, the standard curve is based on the amplification result of FIG. 2. The horizontal axis is the template copy number, and the vertical axis is threshold cycles, which is also the Cq value. According to the standard curve obtained by the real-time PCR reactor (CFX-96, BioRad), it has credible dynamic range with correlation coefficient $R^2$ more than 0.98 and the amplification efficiency (E) between 90% and 100%. If the amplification efficiency as above-mentioned is lower than 90%, it may indicate that the worse primer design cause pool annealing effect, so that the amplification efficiency is low. If the amplification efficiency is higher than 110%, it may indicate that the primers have too many non-specific annealing resulting in high amplification efficiency. As shown in FIG. 3, a straight line with a slope of −3.265 is calculated and presented based on the amount of the template with $10^2$ to $10^8$ copies in FIG. 2, and the correlation coefficient is 0.999 and the amplification efficiency is 102.414%. Therefore, the sensitivity of primers SEQ ID NOs. 1 and 2 is in line with the dynamic range.

Figure 4:
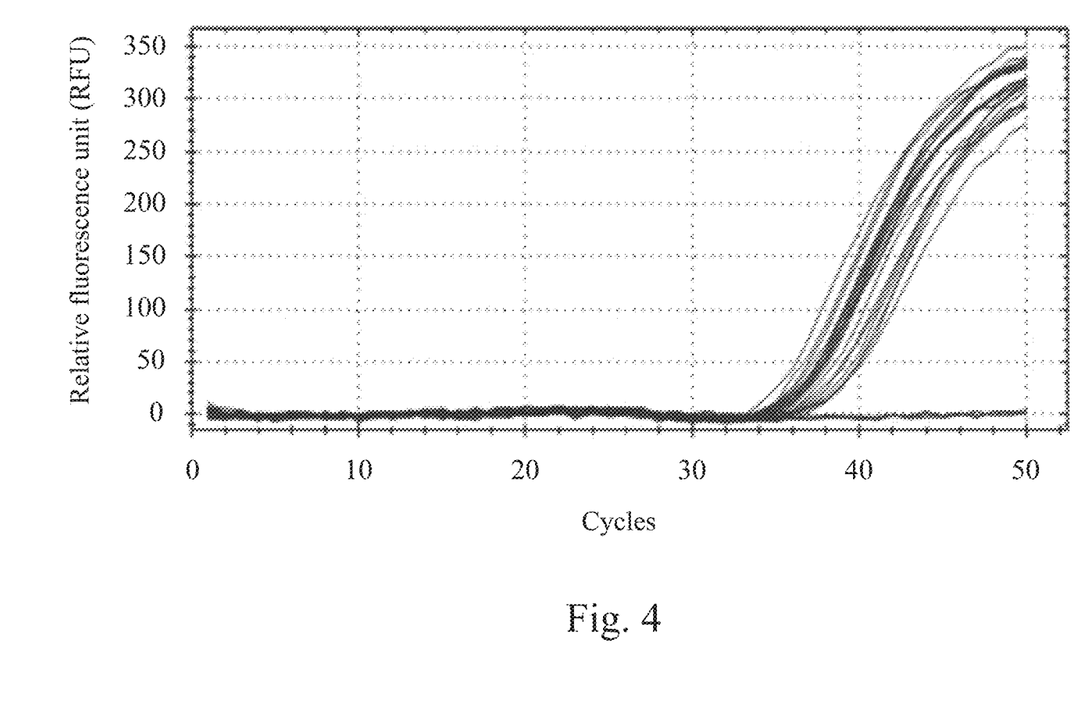
FIG. 4 shows the amplification curve of the real-time PCR performed by the primers SEQ ID NOs. 1 and 2, and the primers are tested under 10 copies of templates according to one embodiment of the present disclosure.

In order to test the sensitivity limitation of the combination of the primers and the probe, the amount of the template with $10^1$ copies and 5 copies were further selected for performing the real-time PCR. The real-time PCR was performed by the primers (SEQ ID NOs. 1 and 2) and the probe (SEQ ID NO. 3), and the real-time PCR was repeated 20 times. The data of the template with $10^1$ copies as shown in FIG. 4 is the amplification curve which is obtained after performing the real-time PCR. The horizontal axis is the number of cycles, and the vertical axis is the relative fluorescence unit (RFU). The amplification curve shows that the fluorescence value of $10^1$ copies is in a positive trend of rising. The amplification results of $10^1$ copies and 5 copies are summarized in Table 2 below.

TABLE 2

| Copies | Cq range | Cq mean | Cq Standard deviation | Replicates | Positive rate (cut off = 40) |
|---|---|---|---|---|---|
| 5 | 34.00-37.7-NA | 35.64 | 1.045 | 20 | 95% |
| 10 | 34.85-36.99 | 36.23 | 0.608 | 20 | 100% |

Table 2 shows that when the amount of template is $10^1$ copies, the threshold is set to 40 cycles (cut off=40). After repeating 20 times, the template is detected every time so that the positive rate is 100%. After detecting, the 20 repeated groups have Cq values ranging from 34.85 to 36.99 with average of 36.23. When the amount of template is 5 copies, the threshold is set to 40 cycles (cut off=40). There is only one time with no detection (N/A) after repeating 20 times, so the positive rate is 95%. The remaining 19 repeated groups have Cq values ranging from 34 to 37.7 with an average of 35.64. The positive rate of above 95% is the confidence interval, so when using the combination of the primers and the probe of the example, a minimum detection limit of the template is 5 copies.

Figure 5:
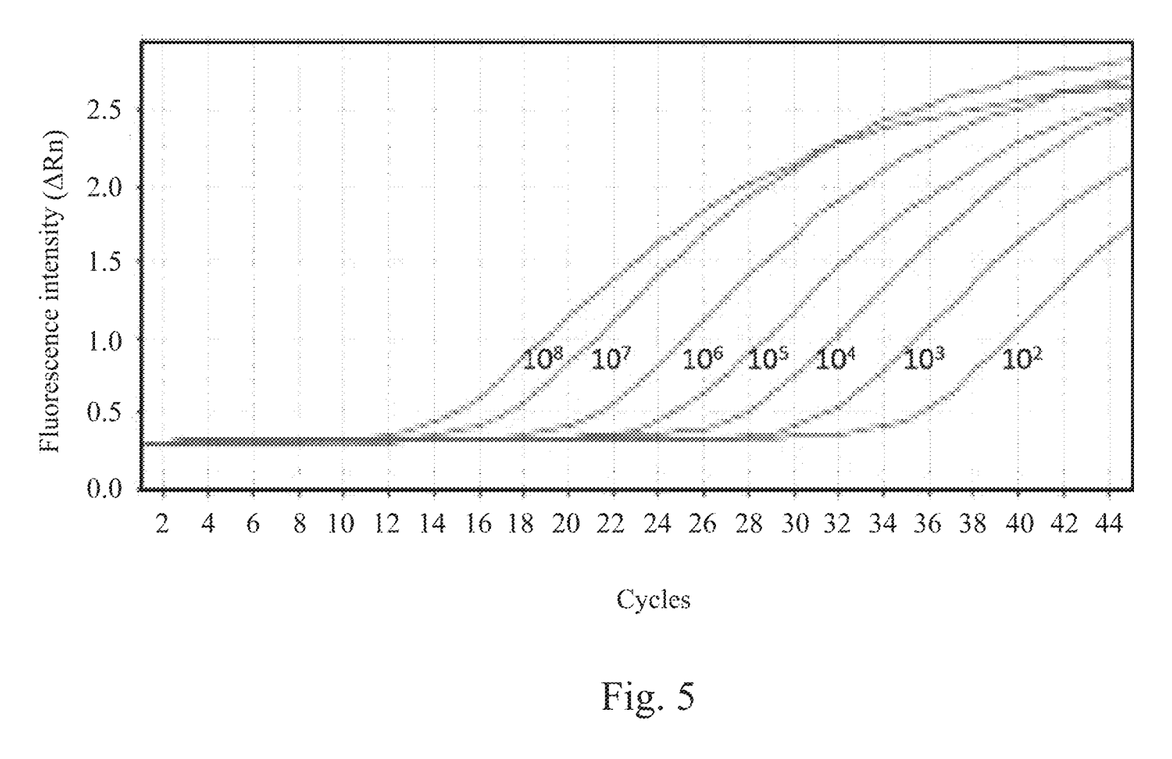
FIG. 5 shows the amplification curve of the real-time PCR performed by the primers similar to SEQ ID NOs. 1 and 2, and the amplification curve shows that the fluorescence value of $10^2$ to $10^8$ copies is in a positive trend of rising.

In addition to further detecting the specificity of SEQ ID NOs. 1 and 2, a pair of similar primers in this example was designed based on the sequences as set forth in SEQ ID NOs. 1 and 2. Specifically, the forward primer of the similar primers was 50% similar to SEQ ID NO. 1, and the reverse primer of the similar primers was 66% similar to SEQ ID NO. 2. Then, the real-time PCR was performer by the similar primers. The detecting method is the same as above-mentioned and not to be further discussed here. As shown in FIG. 5, the amplification curve is obtained after performing the real-time PCR by using the similar primers. The amplification curve shows that the fluorescence value of $10^2$ to $10^8$ copies is in a positive trend of rising. According to the amplification results in FIG. 5, the values are summarized in Table 3 below.

TABLE 3

| | Copies | | | | | | |
|---|---|---|---|---|---|---|---|
| | $10^2$ | $10^3$ | $10^4$ | $10^5$ | $10^6$ | $10^7$ | $10^8$ |
| Cq value | 35.85 | 31.52 | 28.15 | 24.82 | 21.35 | 17.31 | 14.98 |

Table 3 shows that even though SEQ ID NOs. 1 and 2 have certain degree of variation, Cq value still can maintain below 40 cycles (that is 35.85) when the amount of template is lower to $10^2$ copies, and that is slightly higher than SEQ ID NOs. 1 and 2 detecting the same amount of template, 33.19 of Cq value. That is, the sensitivity of the detection is not much difference between the sequences of original primers and the sequences of the primers with certain variation.

Furthermore, in order to further detecting the specificity of the probe SEQ ID NO. 3, a similar probe in this example was designed based on the sequences as set forth in SEQ ID NO. 3. Specifically, the similar probe was SEQ ID NO. 5 which was 75% similar to SEQ ID NO. 3. Then, the real-time PCR was performer by (1) the similar primers (SEQ ID NO. 5) with the primers (SEQ ID NOs. 1 and 2), and (2) the probe (SEQ ID NO. 3) with the primers (SEQ ID NOs. 1 and 2). The detecting method is the same as above-mentioned and not to be further discussed here. The detecting result is shown in Table 4 below.

TABLE 4

| Probe sequence | Copies | Repeat times | Positive rate (cut off = 40) |
|---|---|---|---|
| SEQ ID NO. 3 | 10 | 8 | 100% |
| SEQ ID NO. 5 | 10 | 8 | 100% |

Table 4 shows that when the amount of template is $10^1$ copies, the threshold is set to 40 cycles (cut off=40) either in the group of the probe SEQ ID NO. 3 or the group of the similar probe SEQ ID NO. 5. After repeating 8 times, the templates in both groups are detected every time, so that the positive rates of both groups are 100%. Therefore, even though the probe have certain degree of variation, the positive rate of the similar probe recognizing to the target gene (SEQ ID NO. 4) still maintains at 100%. That is, the sensitivity of the detection is not difference between the original probe sequence and the probe sequence with certain variation.

Clinical Test (A)

Figure 6:
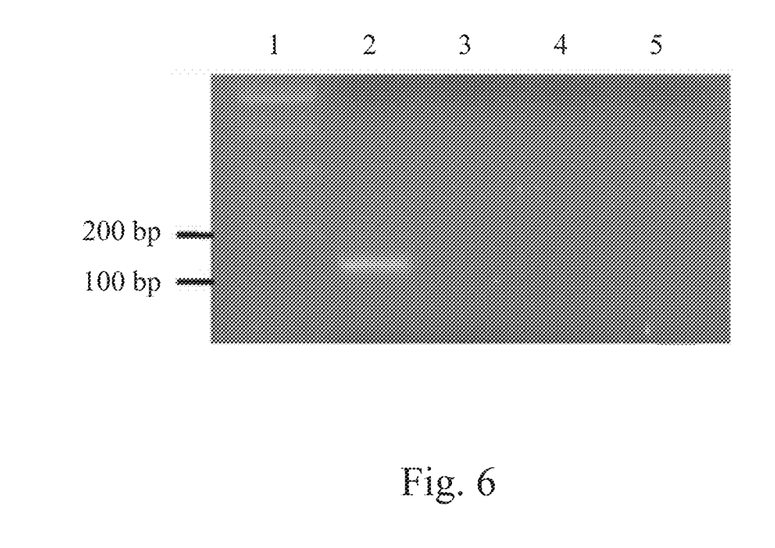
FIG. 6 shows the electrophoresis result of the test with SEQ ID NOs. 1 and 2, according to one embodiment of the present disclosure.

This example was further used for clinical testing. The clinical samples were the sputum of the patients diagnosed with tuberculosis, and the DNAs were extracted from the sputum of the patients. According to the product manual of commercial PCR kit (Dr. Q Taq DNA polymerase, BioFuture), the PCR was performed by the DNA extracted from the tuberculosis patient and the primers with 0.2 µM of SEQ ID NOs. 1 and 2. The conditions of the PCR were 95° C. for 2 minutes, denaturation at 95° C. for 5 seconds and annealing/amplification at 60° C. for 10 seconds, and 25 cycles of the reaction were performed. Then, the product obtained from the PCR was analyzed by electrophoresis. As shown in FIG. 6, lane 1 is marker ladder; lane 2 shows that the amplified product is obtained from the DNA in the sputum of the patient previously diagnosed by the FOR; and lanes 3 to 5 as control show that the product was obtained from the DNA in the sputum of the subject without tuberculosis by the PCR. According to the design of the primers as above-mentioned, the size of the amplified product is expected to be 141 base pairs, and the amplified product of lane 2 is a single band with the size between 100 and 200 base pairs. That is, SEQ ID NOs. 1 and 2 do not generate non-specific amplified product, and the size of the amplified product is in line with the expectation, so that SEQ ID NOs. 1 and 2 can be used in clinical detection.

Clinical Test (B)

After verifying SEQ ID NOs. 1 and 2 which can be used in clinical detection as above-mentioned, SEQ ID NOs. 1 and 2 were compared with a commercial primer pair kit. That is, in this test, the examples refer to the real-time PCR performed by SEQ ID NOs. 1 and 2 of the present embodiment, and the comparative examples refer to the real-time PCR performed by the commercial primer pair kit. As shown in Table 5, clinical examples 1, 2 and 3 are derived from three different patients. Regarding Cq value, the examples are 33.21 to 34.90, and the comparative examples are 42.70 to 45.30. That is, the number of cycles required for detection by the examples can be about 7.8 to 12.09 cycles less than that of the comparative example. In the case of the same amount of template, the sensitivity of the example is significantly better than that of the comparative example.

TABLE 5

| Clinical example | Cq value | |
|---|---|---|
| | Comparative example | Example |
| Clinical example 1 | 42.70 | 33.21 |
| Clinical example 2 | 45.30 | 34.69 |
| Clinical example 3 | 44.80 | 34.90 |

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for detecting presence or absence of *mycobacterium*, comprising steps of:
   providing a sample;
   providing a pair of primers, the primers selected from a group consisting of SEQ ID NO: 1 and SEQ ID NO: 2;
   performing a polymerase chain reaction (PCR) by using the primers and the sample,
   wherein
   when a product obtained by the PCR has a size between 100 and 200 base pairs, the *mycobacterium* is detected;
   when the product is absent, the *mycobacterium* is not detected.

2. The method for detecting presence or absence of *mycobacterium* of claim 1, wherein when the product obtained by the PCR has the size between 100 and 200 base pairs, the sample comprises a clinical sample comprising *Mycobacterium tuberculosis* complex (MTBC).

3. The method for detecting presence or absence of *mycobacterium* of claim 2, wherein the clinical sample is blood, sputum, bronchoalveolar lavage fluid, urine, feces, or a combination thereof.

4. The method for detecting presence or absence of *mycobacterium* of claim 2, wherein the step of performing the PCR by using the primers and the sample comprises amplifying a portion of IS6110 sequence in MTBC by the PCR to obtain the product, wherein the portion of IS6110 sequence is SEQ ID NO. 4.

5. The method for detecting presence or absence of *mycobacterium* of claim 1, further comprising a step of providing a probe, wherein the probe is selected from a group consisting of SEQ ID NO: 3, a sequence having 70% to 99% identity to SEQ ID NO. 3, and a sequence complementary to SEQ ID NO. 3.

6. The method for detecting presence or absence of *mycobacterium* of claim 5, wherein before the step of performing the PCR by using the primers and the sample, the method further comprises a step of:
   hybridizing the probe to the sample.

7. The method for detecting presence or absence of *mycobacterium* of claim 1, wherein the PCR in the step of performing the PCR by using the primers and the sample is a real-time quantitative PCR.

* * * * *